United States Patent
Kang et al.

(10) Patent No.: US 11,993,564 B2
(45) Date of Patent: May 28, 2024

(54) METHOD OF DECOMPOSING PHENOLIC BY-PRODUCTS

(71) Applicant: LG CHEM, LTD., Seoul (KR)

(72) Inventors: Min Suk Kang, Daejeon (KR); Sang Beom Lee, Daejeon (KR); Ji Hyang Son, Daejeon (KR); Chi Hyun Jang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 185 days.

(21) Appl. No.: 17/629,319

(22) PCT Filed: Jun. 15, 2021

(86) PCT No.: PCT/KR2021/007491
§ 371 (c)(1),
(2) Date: Jan. 21, 2022

(87) PCT Pub. No.: WO2022/014876
PCT Pub. Date: Jan. 20, 2022

(65) Prior Publication Data
US 2022/0259125 A1 Aug. 18, 2022

(30) Foreign Application Priority Data

Jul. 17, 2020 (KR) .......................... 10-2020-0088698

(51) Int. Cl.
| | | |
|---|---|---|
| *C07C 37/86* | (2006.01) | |
| *C07C 4/24* | (2006.01) | |
| *C07C 7/10* | (2006.01) | |
| *C07C 37/52* | (2006.01) | |
| *C07C 37/68* | (2006.01) | |
| *C07C 37/72* | (2006.01) | |
| *C07C 45/80* | (2006.01) | |
| *C07C 45/82* | (2006.01) | |

(52) U.S. Cl.
CPC ................ *C07C 37/86* (2013.01); *C07C 4/24* (2013.01); *C07C 7/10* (2013.01); *C07C 37/52* (2013.01); *C07C 37/68* (2013.01); *C07C 37/72* (2013.01); *C07C 45/80* (2013.01); *C07C 45/82* (2013.01)

(58) Field of Classification Search
None
See application file for complete search history.

(56) References Cited

U.S. PATENT DOCUMENTS

| 6,034,282 A | * | 3/2000 | Dyckman | ............... C07C 37/08 |
|---|---|---|---|---|
| | | | | 568/754 |
| 2006/0252975 A1 | * | 11/2006 | Zakoshansky | ..... B01D 11/0446 |
| | | | | 588/405 |
| 2022/0009868 A1 | * | 1/2022 | Kang | ...................... C07C 45/80 |

FOREIGN PATENT DOCUMENTS

| CN | 1132193 A | | 10/1996 | | |
|---|---|---|---|---|---|
| CN | 1137033 A | | 12/1996 | | |
| JP | 08-259481 A | | 10/1996 | | |
| JP | 2005-29478 A | | 2/2005 | | |
| JP | 2005029478 A | * | 2/2005 | ............ | B01D 11/04 |
| JP | 4356339 B2 | | 8/2009 | | |
| JP | 4356377 B2 | | 8/2009 | | |
| KR | 10-0396718 B1 | | 12/2003 | | |
| KR | 10-2019-0058273 A | | 5/2019 | | |
| KR | 10-2020-0077027 A | | 6/2020 | | |
| KR | 10-2020-0077248 A | | 6/2020 | | |
| WO | WO-2021054607 A1 | * | 3/2021 | ............ | B01D 17/02 |

* cited by examiner

*Primary Examiner* — Rosalynd A Keys
(74) *Attorney, Agent, or Firm* — Bryan Cave Leighton Paisner LLP (57) ABSTRACT

Provided is a method of decomposing phenolic by-products, and more particularly, a method of decomposing phenolic by-products including: supplying a phenolic by-product stream to a decomposition device to perform thermal decomposition; separating an upper discharge stream including effective components and a lower discharge stream including materials having a high boiling point in the decomposition device; supplying the lower discharge stream from the decomposition device, a side discharge stream from the decomposition device, and a process water stream to a mixing device and mixing these streams; and supplying a discharge stream from the mixing device to a layer separation device to separate the discharge stream from the mixing device into an oil phase and an aqueous phase.

10 Claims, 3 Drawing Sheets

METHOD OF DECOMPOSING PHENOLIC BY-PRODUCTS

CROSS-REFERENCE TO RELATED APPLICATIONS

The present application is a National Phase entry pursuant to 35 U.S.C. § 371 of International Application No. PCT/KR2021/007491, filed on Jun. 15, 2021, and claims the benefit of and priority to Korean Patent Application No. 10-2020-0088698, filed on Jul. 17, 2020, the entire contents of which are incorporated by reference in their entirety for all purposes as if fully set forth herein.

TECHNICAL FIELD

The present invention relates to a method of decomposing phenolic by-products, and more particularly, to a method of reducing occurrence of fouling in a reboiler of a decomposition device without energy loss, separating effective components and materials having a high boiling point from the phenolic by-products, and desalting the separated material having a high boiling point to facilitate utilization of the material having a high boiling point.

BACKGROUND ART

About 95% of phenols used around the world are generally produced by a Hock process. The Hock process is carried out by three steps of: (1) alkylating benzene by propylene to form cumene, (2) binding the cumene with oxygen to oxidize cumene to cumene hydroperoxide (CHP), and (3) decomposing cumene hydroperoxide into phenol and acetone by an acid decomposition reaction in the presence of an acid catalyst.

Here, in step (2) of oxidizing cumene, by-products such as acetophenone (AP), dimethyl benzyl alcohol (DMBA), dicumyl peroxide (DCP), and dicumene (DC) are produced, in addition to cumene hydroperoxide.

In addition, in step (3) of acid decomposition reaction of cumene hydroperoxide, hydroxy acetone (HA), 2-methylbenzofuran (2-MBF), α-methylstyrene (AMS), mesityl oxide (MO), an α-methylstyrene dimer (AMS dimer), cumylphenol (CP), and the like are produced as by-products, in addition to phenol and acetone.

Therefore, since a product stream produced by the reaction process described above is present in a state in which phenol, acetone, and various by-products are mixed, a series of separation processes for separating phenol from the product stream is required.

The product stream is introduced to a separate separation device, in which an acetone-based mixture including unreacted cumene, acetone, α-methylstyrene, hydroxyacetone, and the like is separated in the tower top of the separation device and a phenolic mixture including phenol, a part of α-methylstyrene and 2-methylbenzofuran, other by-products, and the like is separated in the tower bottom of the separation device.

The phenolic mixture separated from the tower bottom of the separation device is introduced to a phenol column, in which phenol is separated in the tower top of the phenol column and phenolic by-products such as dicumyl peroxide, cumylphenol, α-methylstyrene dimer, and tar are separated in the tower bottom of the phenol column.

In addition, in general, a process of producing bisphenol A (BPA) is a process of condensing phenol and acetone produced from the Hock process in the presence of an acidic catalyst or a cation exchange resin to produce bisphenol A.

Thus, unreacted phenol, unreacted acetone, trisphenol (BPX), tar, and the like are produced as by-products, in addition to bisphenol A, in the bisphenol A reaction product stream.

From the by-products produced in the phenol process and the bisphenol A preparation process, effective components such as phenol, cumene, and α-methylstyrene may be recovered by a separate decomposition device, and a study of the decomposition process and the decomposition device allowing efficient recovery of the effective components is in progress.

DISCLOSURE

Technical Problem

In order to solve the problems mentioned in the Background Art, an object of the present invention is to provide a method of reducing occurrence of fouling in a reboiler of a decomposition device in the decomposition of phenolic by-products, obtaining high-valued effective components, and separating and desalting materials having a high boiling point to facilitate the utilization thereof.

Technical Solution

In one general aspect, a method of decomposing phenolic by-products includes: supplying a phenolic by-product stream to a decomposition device to perform thermal decomposition; separating an upper discharge stream including effective components and a lower discharge stream including materials having a high boiling point in the decomposition device; supplying the lower discharge stream from the decomposition device, a side discharge stream from the decomposition device, and a process water stream to a mixing device and mixing these streams; and supplying a discharge stream from the mixing device to a layer separation device to separate the discharge stream from the mixing device into an oil phase and an aqueous phase.

Advantageous Effects

When phenolic by-products are decomposed by the method of decomposing phenolic by-products according to the present invention, materials having a high boiling point which are utilized as high-valued effective components and fuels can be obtained.

In addition, since almost no process water is present in the phenolic by-products, occurrence of fouling in a reboiler of the decomposition device can be prevented.

In addition, salt removal efficiency is improved by removing salts included in the lower discharge stream from the decomposition device where the materials having a high boiling point is separated using the side discharge stream from the decomposition device, and occurrence of fouling in the device can be prevented by using the materials having a high boiling point from which salts are removed as a fuel.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "stream" may refer to a fluid flow in a process, or may refer to a fluid itself flowing in a pipe. Specifically, the "stream" may refer to both a fluid itself flowing in a pipe connecting each device and a fluid flow. In addition, the fluid may refer to a gas or a liquid.

Hereinafter, the present invention will be described in more detail with reference to the FIG. 1 for better understanding of the present invention.

According to the present invention, a method of decomposing phenolic by-products is provided. The method of decomposing phenolic by-products can include: supplying a phenolic by-product stream to a decomposition device and performing thermal decomposition; separating an upper discharge stream including effective components and a lower discharge stream including materials having a high boiling point in the decomposition device; supplying the lower discharge stream from the decomposition device, a side discharge stream from the decomposition device, and a process water stream to a mixing device and mixing these streams; and supplying a discharge stream from the mixing device to a layer separation device to separate the discharge stream from the mixing device into an oil phase and an aqueous phase.

According to an exemplary embodiment of the present invention, the phenolic by-products can include any one or more of phenolic by-products produced in a phenol preparation process and phenolic by-products produced in a bisphenol A preparation process. For example, the phenolic by-products can be phenolic by-products produced in the phenol preparation process, phenolic by-products produced in the bisphenol A preparation process, or a mixture of the phenolic by-products produced in the phenol preparation process and the phenolic by-products produced in the bisphenol A preparation process. More specifically, the phenolic by-products can be a mixture of phenolic by-products produced in a phenol preparation process and phenolic by-products produced in a bisphenol A preparation process.

The phenol preparation process can be carried out by the Hock process described above. Specifically, the phenol preparation process can be carried out by a step of decomposing and purifying cumene hydroperoxide prepared by an oxidation reaction of cumene and separating phenol and acetone. The step of decomposing and purifying cumene hydroperoxide prepared by the oxidation reaction of cumene to separate phenol and acetone is a step of using a cumene purification process and a phenol/acetone purification process. First, propylene and benzene are alkylated to prepare cumene and then heavy/light by-products are discharged by a purification process and cumene is purified and separated. Subsequently, the purified cumene is oxidized to prepare cumene hydroperoxide (CHP), the cumene hydroperoxide (CHP) is decomposed under a common acid catalyst such as sulfuric acid ($H_2SO_4$) to produce phenol, acetone, α-methylstyrene (AMS), and heavy by-products, and through a purification process, α-methylstyrene (AMS) and heavy by-products are discharged and phenol and acetone are purified and separated.

Since a product stream produced by the reaction process described above is present in a state in which phenol, acetone, and various by-products are mixed, a series of separation processes for separating phenol from the product stream is required.

The product stream is introduced to a separate separation device, in which an acetone-based mixture including unreacted cumene, acetone, α-methylstyrene, hydroxyacetone, and the like is separated in the tower top of the separation device and a phenolic mixture including phenol, a part of α-methylstyrene and 2-methylbenzofuran, other by-products, and the like is separated in the tower bottom of the separation device.

The phenolic mixture separated from the tower bottom of the separation device is introduced to a phenol column, in which phenol is separated in the tower top of the phenol column and phenolic by-products such as dicumyl peroxide, cumylphenol, α-methylstyrene dimer, and tar are separated in the tower bottom of the phenol column. As a result, the phenolic by-products produced from the phenol preparation process can include some effective components such as phenol, cumene, and α-methylstyrene, and tar.

In addition, the bisphenol A preparation process can be carried out by a method of reacting phenol and acetone prepared by the Hock process described above to prepare bisphenol A, and recovering bisphenol A from the reaction product. Specifically, the bisphenol A preparation process can be carried out by decomposing and purifying cumene hydroperoxide prepared by an oxidation reaction of cumene to separate phenol and acetone; separating bisphenol A prepared by reacting the separated phenol and acetone and decomposing a stream including unseparated bisphenol A under an aqueous alkaline solution; and separating the reaction product by the decomposition reaction, phenolic by-products, and acetone-based by-products.

The step of decomposing and purifying cumene hydroperoxide prepared by the oxidation reaction of cumene to separate phenol and acetone is a step of using a cumene purification process and a phenol/acetone purification process. First, propylene and benzene are alkylated to prepare cumene and then heavy/light by-products are discharged by a purification process and cumene is purified and separated. Subsequently, the purified cumene is oxidized to prepare cumene hydroperoxide (CHP), the cumene hydroperoxide (CHP) is decomposed under a common acid catalyst such as sulfuric acid ($H_2SO_4$) to produce phenol, acetone, α-methylstyrene (AMS), and heavy by-products, and through a purification process, α-methylstyrene (AMS) and heavy by-products are discharged and phenol and acetone are purified and separated.

The step of separating bisphenol A prepared by reacting the separated phenol and acetone and decomposing a stream including unseparated bisphenol A under an aqueous alkaline solution is a step of using a bisphenol A (BPA) purification process. First, the purified and separated phenol and acetone are reacted to prepare bisphenol A, more correctly crude bisphenol A, and then a crystallization process was carried out to prepare bisphenol A having an improved purity. Bisphenol A prepared as such is separated by a BPA purification process and by-products including unseparated bisphenol A are decomposed under an excessive amount of the aqueous alkaline solution having properties of a base such as NaOH, KOH, and LiOH.

In the step of separating the reaction product by the decomposition reaction, phenolic by-products, and acetone-based by-products, the stream after the decomposition reaction can be supplied to a separation device to separate an acetone-based mixture in a tower top of the separation device and separate a reaction product in a tower bottom of the separation device. The reaction product is introduced to a bisphenol A/phenol column where bisphenol A is separated in the tower top, and phenolic by-products such as bisphenol A, phenol, dicumyl peroxide, cumylphenol, an α-methylstyrene dimer, and tar are separated in the tower bottom. Here, the phenolic by-products include bisphenol A which is a product, and effective components such as cumene and α-methylstyrene, in addition to tar which is an impurity.

As a result, the phenolic by-products produced from the bisphenol A preparation process can include some effective components such as phenol, cumene, and α-methylstyrene, and materials having a high boiling point such as tar.

Therefore, a mixture of the phenolic by-products produced in the bisphenol A preparation process and phenolic by-products produced in the phenol preparation process can include one or more selected from the group consisting of bisphenol A, phenol, α-methylstyrene, acetophenone, cumylphenol, and an α-methylstyrene dimer. As a specific example, the phenolic by-products can include two or more selected from the group consisting of bisphenol A, phenol, α-methylstyrene, acetophenone, cumylphenol, and an α-methylstyrene dimer, or all of them.

The phenolic by-products can include the phenolic by-products produced in the bisphenol A preparation process and the phenolic by-products produced in the phenol preparation process at a flow rate ratio of 1:2 to 10. For example, the phenolic by-products can include the phenolic by-products produced in the bisphenol A preparation process and the phenolic by-products produced in the phenol preparation process at a flow rate ratio of 1:2 to 10, 1:4 to 10, or 1:6 to 10. As such, it can be preferred to decompose phenolic by-products having a high content of the phenolic by-products produced in the phenol preparation process relative to the phenolic by-products produced in the bisphenol A preparation process, in terms of preventing a load on the decomposition device 100 and reducing an amount of energy used in the process.

According to an exemplary embodiment of the present invention, the phenolic by-product stream can be supplied to the decomposition device 100 and thermally decomposed. The decomposition carried out in the decomposition device 100 can be thermal decomposition, and the decomposition device 100 for carrying out this can be a thermal cracker. As a specific example, the thermal cracker can be a reactor-distillation tower integrated separation device.

The effective components are separated from the upper portion of the decomposition device 100, and for effectively separating the materials having a high boiling point including tar from the lower portion, the decomposition device 100 can be operated at a temperature of 260° C. to 370° C., 290° C. to 370° C., or 300° C. to 350° C. and a pressure of 0.1 bar to 3 bar, 0.1 bar to 2 bar, or 0.1 bar to 1.0 bar.

In the decomposition device 100, the effective components can be separated from the upper discharge stream. The effective components can include one or more selected from the group consisting of, for example, phenol, α-methylstyrene, and cumene. In addition, the lower discharge stream from the decomposition device 100 is a stream including tar, and may be recovered and reused as a fuel of a boiler and the like.

Since the phenolic by-products includes phenolic by-products discharged in a phenol preparation process and a bisphenol A preparation process, a trace of salts may be included due to an acid decomposition reaction of cumene hydroperoxide. Since the salts may be included in the lower discharge stream from the decomposition device 100 where materials having a high boiling point such as tar are separated, when the materials having a high boiling point including salts are used as a fuel of a boiler and the like, fouling in the boiler may be caused.

In order to remove the salts in the phenolic by-products, the phenolic by-product stream is subjected to a desalting process before being supplied to the decomposition device 100, and an oil phase from which salts are removed by the desalting process can be supplied to the decomposition device as the phenolic by-product and thermally decomposed, but in this case, 2.5 wt % to 5 wt % of process water can remain in the oil phase separated in the desalting process. The process water remaining in the phenolic by-products as such is partly evaporated when the process water passes through a reboiler 110 of the decomposition device 100 later during the decomposition of phenolic by-products for obtaining effective components from the phenolic by-products, and causes fouling due to the deposition of an aqueous salt. In addition, in this case, cooling should be performed for desalting phenolic by-products at a high temperature produced in the phenol preparation process and the bisphenol preparation process, and an amount of energy used for supplying an oil stream at a low temperature after the desalting process to the decomposition device 100 and heating the stream is increased. In addition, though a separate preheater can be provided for reducing energy for heating in the decomposition device 100, the process becomes complicated, and investment costs and equipment maintenance costs increase.

Therefore, in the present invention, the content of the process water is 2.0 wt % or less, 0.01 wt % to 1.5 wt %, or 0.101 wt % to 0.5 wt %, and thus, phenolic by-products in which almost no process water is present, discharged from the phenol preparation process and the bisphenol A preparation process can be directly supplied to the decomposition device 100 and decomposed. Thus, occurrence of fouling in the reboiler 110 of the decomposition device 100 can be prevented, and the lower discharge stream of the decomposition device 100 including the materials having a high boiling point is desalted, thereby also preventing occurrence of fouling in the boiler when using the materials having a high boiling point as a fuel of the boiler and the like later.

According to an exemplary embodiment of the present invention, the lower discharge stream of the decomposition device 100 can be subjected to a desalting process. Specifically, the lower discharge stream of the decomposition device 100 is supplied to a mixing device 200, and the side discharge stream from the decomposition device 100 and the process water can be mixed in the mixing device 200.

The process water is for dissolving salts in the phenolic by-product stream therein and removing the salts, and may mean including all various aqueous solutions such as an acidic aqueous solution and a basic aqueous solution, in addition to distilled water.

The process water can have a pH of 3.5 to 7, 3.5 to 5.5, or 3.5 to 4.5, and within the range, corrosion of the mixing device 200 and a layer separation device 300 is prevented, solubility of the salts is improved, and phase separation ability in separation into an oil phase and an aqueous phase in the layer separation device can be improved.

The mixing device 200 can be a mixer for mixing the lower discharge stream from the decomposition device 100, the side discharge stream from the decomposition device 100, and the process water stream. As a specific example, the mixer can be provided with a line mixer or a static mixer for easily carrying out mixing of the lower discharge stream from the decomposition device 100, the side discharge stream from the decomposition device 100, and the process water stream.

The side discharge stream from the decomposition device 100 can be discharged at 25% to 90%, 40% to 90%, or 50% to 90% of the total number of stages of the decomposition device 100. In this case, acetophenone discharged to the upper discharge stream from the decomposition device 100 can be significantly reduced.

The side discharge stream from the decomposition device 100 can include 40 wt % or more of acetophenone. For example, the side discharge stream from the decomposition device 100 can include 40 wt % to 99 wt %, 55 wt % to 99 wt %, or 60 wt % to 99 wt % of acetophenone. The acetophenone is an organic material included in the phenolic by-product stream, and since it acts as an impurity in contrast to the effective components obtained by the phenolic by-product decomposition reaction, it is preferred to minimize the content of acetophenone in the effective components. Therefore, when according to the present invention, the side discharge stream from the decomposition device 100 includes 40 wt % or more of acetophenone, the side discharge stream from the decomposition device 100 can be separated to minimize the content of acetophenone in the effective components obtained by the phenolic by-product decomposition reaction, and thus, it is advantageous for obtaining the effective components. In addition, the side discharge stream having a high content of acetophenone from the decomposition device 100 is supplied to the mixing device 200 and used as an aid of the desalting process of the lower discharge stream from the decomposition device 100, thereby activating phase separation between an oil phase and an aqueous phase including salts to minimize salts remaining in the oil phase.

In addition, the side discharge stream from the decomposition device 100 and the lower discharge stream from the decomposition device 100 form a mixed stream, and the mixed stream can be supplied to the mixing device 200. In this case, flowability of the lower discharge stream from the decomposition device 100 having a bad flowability due to a high tar content can be improved. Specifically, the side discharge stream of the decomposition device 100 is used to decrease the viscosity of the lower discharge stream from the decomposition device 100 to improve flowability.

The mixed stream of the side discharge stream from the decomposition device 100 and the lower discharge stream from the decomposition device 100 is a stream discharged from the decomposition device 100 operated at a high temperature and may be hot. Therefore, in order to prevent vaporization of the process water before supplying the mixed stream to the mixing device 200, the mixed stream should be cooled. Specifically, the mixed stream can be cooled using a separate cooler 400, and then supplied to the mixed device 200 and mixed with the process water.

A portion of the upper discharge stream from the decomposition device 100 passes through the reboiler 110 and is circulated to the decomposition device 100, and the residual stream can be supplied to the mixing device 200.

According to an exemplary embodiment of the present invention, a flow rate ratio of the lower discharge stream from the decomposition device 100, the side discharge stream from the decomposition device 100, and the process water stream supplied to the mixing device 200 can be 1:0.2 to 0.8:1 to 3, 1:0.3 to 0.7:1.2 to 2.8, or 1:0.4 to 0.6:1.3 to 1.8. The flow rate ratio of the lower discharge stream from the decomposition device 100, the side discharge stream from the decomposition device 100, and the process water stream is controlled to the above range, thereby improving not only mixing the lower discharge stream from the decomposition device 100, the side discharge stream from the decomposition device 100 but also phase separation ability into an oil phase and an aqueous phase in the layer separation device 300 described later, and the process water stream but also removal efficiency of salts included in the lower discharge stream from the decomposition device 100.

According to an exemplary embodiment of the present invention, the discharge stream from the mixing device 200 is supplied to the layer separation device 300, and can be phase-separated into an oil phase and an aqueous phase in the layer separation device 300. Specifically, in the layer separation device 300, salts included in the lower discharge stream from the decomposition device 100 can be removed, and the oil phase including the materials having a high boiling point from which salts are removed and an aqueous phase including salts can be phase-separated.

The oil stream discharged from the layer separation device 300 includes the materials having a high boiling point from which salts are removed, and the materials having a high boiling point can be recovered from the oil stream discharged from the layer separation device 300. The materials having a high boiling point recovered above can be used as a fuel of a boiler and the like, and in this case, since salts in the materials having a high boiling point are removed, occurrence of fouling in the boiler can be prevented.

A portion of the aqueous stream discharged from the layer separation device 300 can be supplied to the mixing device 200 and the residual stream can be discharged as waste water including salts.

The layer separation device 300 can be a drum for phase-separating the oil phase and the aqueous phase.

For phase-separating the oil phase and the aqueous phase from the layer separation device 300, a step of retaining the discharge stream from the mixing device 200 in the layer separation device 300 for 1 hour to 10 hours, 2 hours to 8 hours, or 4 hours to 6 hours, can be included. As such, when the stream discharged from the mixing device 200 is retained in the layer separation device 300, phase separation can occur more clearly, and thus, salts in the lower discharge stream from the decomposition device 100 can be removed as much as possible.

According to an exemplary embodiment of the present invention, in the method of decomposing phenolic by-products, if necessary, devices such as a distillation column (not shown), a condenser (not shown), a reboiler (not shown), a valve (not shown), a pump (not shown), a separator (not shown), and a mixer (not shown) can be further installed.

Hereinabove, the method of decomposing phenolic by-products according to the present invention has been described and illustrated in the drawings, but the description and the illustration in the drawings are the description and the illustration of only core constitutions for understanding of the present invention, and in addition to the process and apparatus described above and illustrated in the drawings, the process and the apparatus which are not described and illustrated separately may be appropriately applied and used for carrying out the method of decomposing phenolic by-products according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES

Example 1

Figure 1:
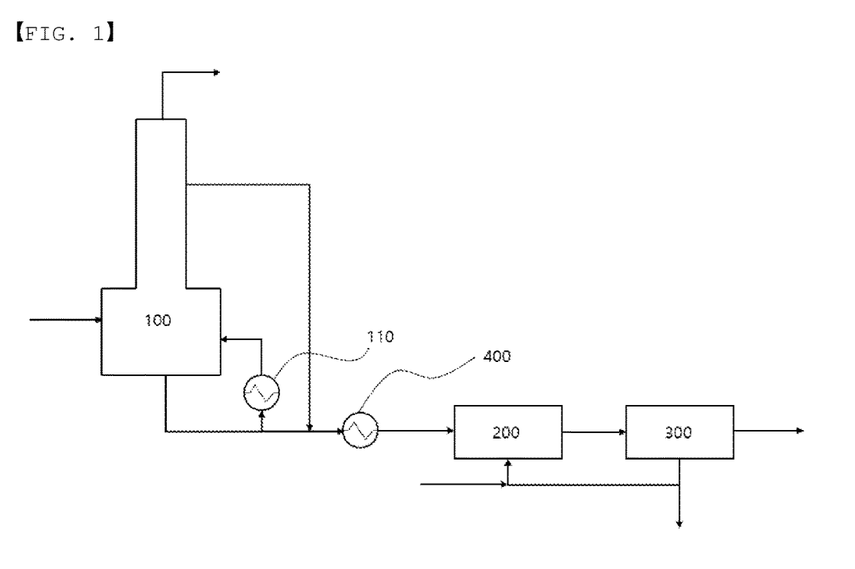
FIG. 1 is a process flow diagram of a method of decomposing phenolic by-products, according to an exemplary embodiment of the present invention.

Referring to the process flow diagram illustrated in FIG. 1, the process was simulated, using an Aspen Plus simulator from Aspen Technology, Inc. Specifically, a phenolic by-product stream at 211° C. having the composition described in Table 1 was supplied to a decomposition device 100 at a flow rate of 1000 kg/hr and thermally decomposed, and effective components were obtained from an upper discharge stream. Here, the operation pressure of the decomposition device 100 was normal pressure, and the operation temperature thereof was controlled to 330° C. In addition, the compositions of the side discharge stream and the lower discharge stream from the decomposition device 100 are shown in the following Table 2.

The lower discharge stream and the side discharge stream from the decomposition device 100 formed a mixed stream, which was cooled to 90° C. via a cooler 400, then supplied to a mixing device 200, and mixed with a process water stream at pH 4 supplied to the mixing device 200. Here, a portion of the lower discharge stream from the decomposition device 100 was circulated to the decomposition device 100 via a reboiler 110, and the residual stream formed a mixed stream with the side discharge stream from the decomposition device 100 and was supplied to the mixing device 200 via the cooler 400. In addition, a flow rate ratio of the lower discharge stream from the decomposition device 100: the side discharge stream from the decomposition device 100: the process water stream which are mixed in the mixing device 200 was controlled to 1:0.5:1.5.

The temperature of the mixed stream was confirmed to be 270° C., and the mixed stream was cooled to 90° C. via the cooler 400 and then was supplied to a layer separation device 300 via the mixing device 200, to be separated into an oil phase and an aqueous phase.

After being retained in the layer separation device 300 for 5 hours, materials having a high boiling point including tar were obtained from the discharged oil stream, a portion of the aqueous stream was circulated to the mixing device 200, and the residual stream was discharged as waste water.

TABLE 1

| Classification | | Phenolic by-products |
|---|---|---|
| Phenol | (wt %) | 4.85 |
| α-Methylstyrene | (wt %) | 7.14 |
| Cumene | (wt %) | 0.00 |
| Acetophenone | (wt %) | 11.60 |
| Cumyl phenol | (wt %) | 15.32 |
| α-Methylstyrene dimer | (w t%) | 10.74 |
| Bisphenol A | (wt %) | 11.56 |
| Others | (wt %) | 38.79 |
| Total | (wt %) | 100.00 |

TABLE 2

| Classification | | Upper discharge stream | Lower discharge stream |
|---|---|---|---|
| Phenol | (wt %) | 32.99 | 19.87 |
| α-Methylstyrene | (wt %) | 50.07 | 5.92 |
| Cumene | (wt %) | 11.83 | 0.94 |
| Acetophenone | (wt %) | 0.01 | 46.75 |
| Isopropyl phenol | (wt %) | 0.00 | 26.19 |
| Others | (wt %) | 5.10 | 0.33 |
| Total | (wt %) | 100.00 | 100.00 |

Example 2

The process was carried out in the same manner as in Example 1, except that the flow rate ratio of the lower discharge stream from the decomposition device 100:the side discharge stream from the decomposition device 100: the process water stream was controlled to 1:0.3:1.3.

COMPARATIVE EXAMPLE

Comparative Example 1

Figure 2:
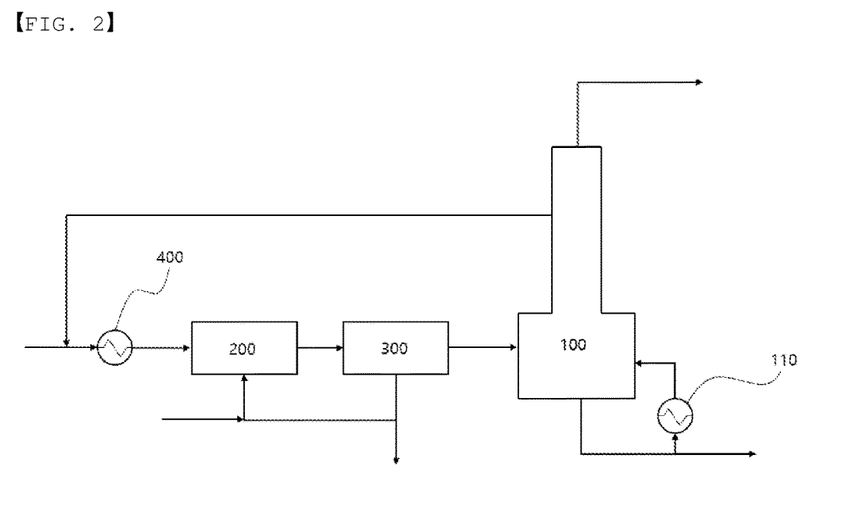
FIGS. 2 to 5 are process flow diagrams for methods of decomposing phenolic by-products according to the comparative examples, respectively.

Referring to the process flow diagram illustrated in FIG. 2, the process was simulated, using an Aspen Plus simulator from Aspen Technology, Inc. Specifically, a phenolic by-product stream at 211° C. having the composition described in Table 1 at a flow rate of 1000 kg/hr formed a mixed stream with the side discharge stream from the decomposition device 100, and the mixed stream was passed through the cooler 400 to be cooled to 90° C., was supplied to the mixing device 200, and was mixed with the process water at pH 4 supplied to the mixing device 200.

A flow rate ratio of the phenolic by-product stream:the side discharge stream from the decomposition device 100: the process water stream was controlled to 1:0.5:1.5.

The discharge stream from the mixing device 200 was supplied to a layer separation device 300 and retained for 5 hours in the layer separation device 300, and an oil stream discharged therefrom was supplied to the decomposition device 100.

Effective components were obtained from the upper discharge stream from the decomposition device 100, and a portion of the lower discharge stream was circulated to the decomposition device 100 via the reboiler 110 and the residual stream was discharged.

Comparative Example 2

Figure 3:
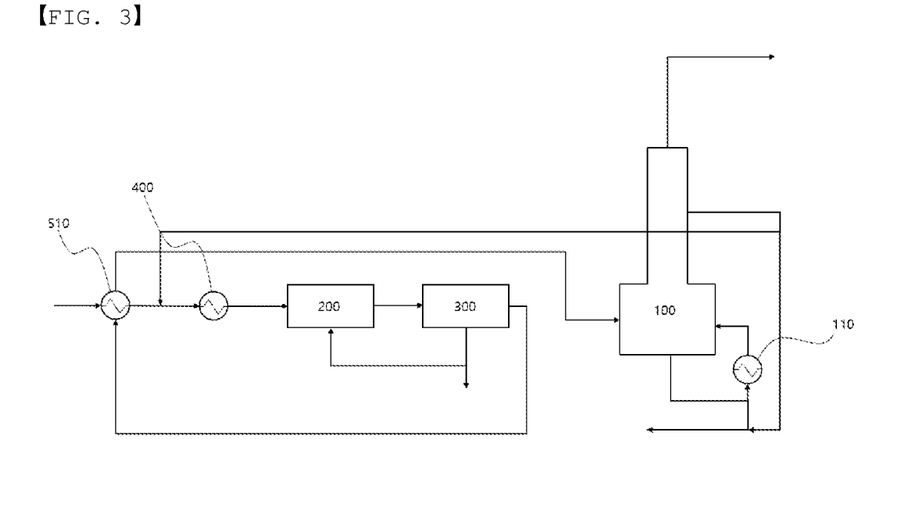

Referring to the process flow diagram illustrated in FIG. 3, the process was simulated, using an Aspen Plus simulator from Aspen Technology, Inc. Specifically, a phenolic by-product stream at 211° C. having the composition described in Table 1 at a flow rate of 1,000 kg/hr was passed through a first preheater 510 and formed a mixed stream with the first stream of the side discharge stream of the decomposition device 100, and the mixed stream was passed through the cooler 400 and supplied to the mixing device 200 in a state of being cooled to 90° C., and was mixed with a process water stream at pH 4 in the mixing device 200. A flow rate ratio of the phenolic by-product stream:the first stream of the side discharge stream from the decomposition device 100: the process water stream which were mixed in the mixing device 200 was controlled to 1:0.5:1.5.

The discharge stream from the mixing device 200 was supplied to the layer separation device 300 and retained for 5 hours in the layer separation device 300, and then an oil stream at 136° C. discharged therefrom was supplied to the decomposition device 100 via the first preheater 510.

Effective components were obtained from the upper discharge stream from the decomposition device 100, a portion of the lower discharge stream was circulated to the decomposition device 100 via the reboiler 110, and the residual stream was mixed with the second stream of the side discharge stream from the decomposition device 100 and discharged.

Comparative Example 3

Figure 4:
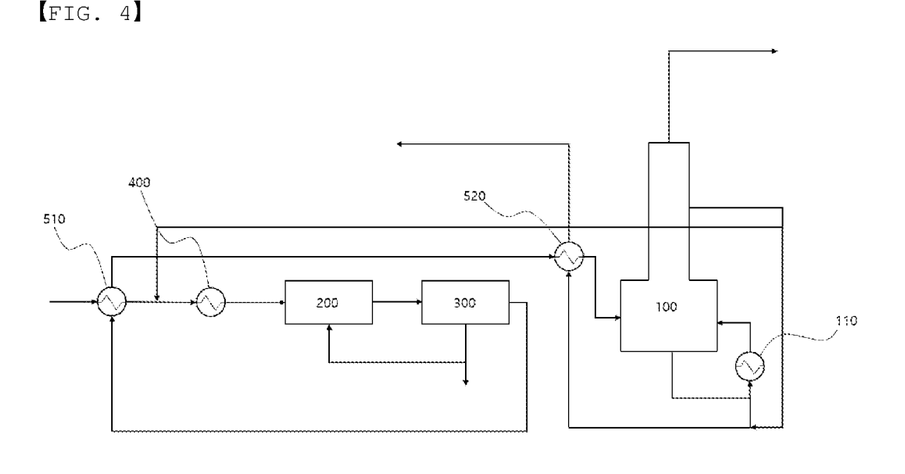

Referring to the process flow diagram illustrated in FIG. 4, the process was simulated, using an Aspen Plus simulator from Aspen Technology, Inc. Specifically, a phenolic by-product stream at 211° C. having the composition described in Table 1 at a flow rate of 1,000 kg/hr was passed through a first preheater 510 and formed a mixed stream with the first stream of the side discharge stream of the decomposition device 100, and the mixed stream was passed through the cooler 400 and supplied to the mixing device 200 in a state of being cooled to 90° C., and was mixed with a process water stream at pH 4 in the mixing device 200. A flow rate ratio of the phenolic by-product stream:the first stream of the side discharge stream from the decomposition device 100: the process water stream which were mixed in the mixing device 200 was controlled to 1:0.5:1.5.

The discharge stream from the mixing device 200 was supplied to a layer separation device 300 and retained for 5 hours in the layer separation device 300, and an oily stream discharged therefrom at 190° C. was supplied to the decomposition device 100 via the first preheater 510 and a second preheater 520.

Effective components were obtained from the upper discharge stream from the decomposition device 100, a portion of the lower discharge stream was circulated to the decomposition device 100 via the reboiler 110, and the residual stream was mixed with the second stream of the side discharge stream from the decomposition device 100, passed through the second preheater 520, and discharged.

Comparative Example 4

Figure 5:
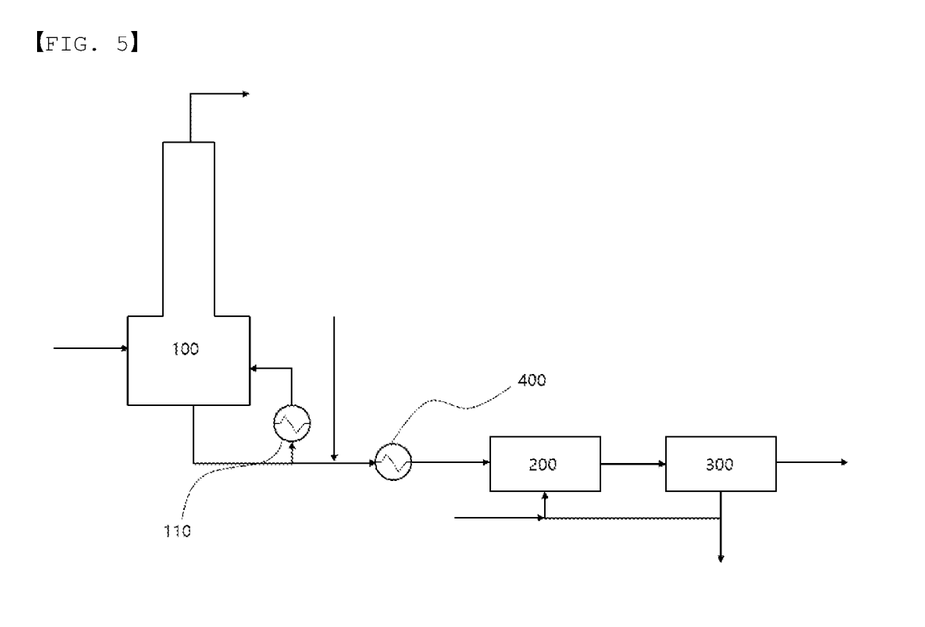

Referring to the process flow diagram illustrated in FIG. 5, the process was simulated, using an Aspen Plus simulator from Aspen Technology, Inc. Specifically, the process was performed in the same manner as in Example 1, except that the lower discharge stream from the decomposition device 100 was mixed with not the side discharge stream from the decomposition device 100 but the phenolic by-product stream produced in the bisphenol A preparation process having the composition of the following Table 3.

TABLE 3

| Classification | | Phenolic by-products |
|---|---|---|
| Phenol | (wt %) | 10.80 |
| Bisphenol A | (wt %) | 58.00 |
| Others | (wt %) | 31.20 |
| Total | (wt %) | 100.00 |

EXPERIMENTAL EXAMPLES

Experimental Example 1

A salt content (ppm) and a salt removal rate (%) in the discharge streams from the mixing device 200 supplied to the layer separation device 300 and the oil stream discharged after removing salts from the layer separation device 300, and an energy requirement amount per ton (Mcal/ton) used in the decomposition device 100, in Examples 1 and 2 and Comparative Examples 1 to 4, were measured, and are shown in the following Table 4:

TABLE 4

| | | Example 1 | Example 2 | Comparative Example 1 | Comparative Example 2 | Comparative Example 3 | Comparative Example 4 |
|---|---|---|---|---|---|---|---|
| Salt content (ppm) | Discharge stream from mixing device | 640 | 900 | 380 | 380 | 380 | 640 |
| | Oil stream | 100 | 180 | 75 | 75 | 75 | 352 |
| Salt removal rate (%) | | 84 | 80 | 80 | 80 | 80 | 45 |
| Energy requirement amount per ton (Mcal/ton) | | 66 | 100 | 195 | 164 | 123 | 66 |

Referring to Table 4, in Examples 1 and 2 in which the phenolic by-products were decomposed by the method according to the present invention, the desalting process was designed in the latter stage of the decomposition process, thereby preventing energy loss caused by cooling phenolic by-products and heating them again without a change in a salt removal rate, and a preheater is not further provided, thereby reducing investment coasts and equipment maintenance costs.

In comparison, in Comparative Example 1 in which the desalting process was designed in the former stage of the decomposition process without installation of an additional preheater, it was confirmed that an energy requirement amount per ton used in the decomposition device 100 was significantly increased.

In addition, in Comparative Examples 2 and 3 in which one and two preheaters were additionally installed, respectively, and the desalting process was designed in the former stage of the decomposition process, the energy requirement amount per ton used in the decomposition device 100 was decreased as compared with Comparative Example 1, but an energy consumption was shown to be higher than those of the Examples, and investment costs and equipment maintenance costs were increased due to installation of the preheater.

In addition, in Comparative Example 4, the desalting process was designed in the latter stage of the decomposition process like the present invention, so that a problem from additional preheater installation and the energy requirement amount in the decomposition device 100 were not additionally arisen, but during the desalting process of the lower discharge stream from the decomposition device 100, the side discharge stream from the decomposition device 100 was not mixed therewith, thereby decreasing salt removal efficiency.

The invention claimed is:

1. A method of decomposing phenolic by-products, the method comprising:
   supplying a phenolic by-product stream having an amount of process water of 2 wt % or less to a decomposition device to perform thermal decomposition;
   separating an upper discharge stream including effective components and a lower discharge stream including materials having a high boiling point in the decomposition device;
   supplying the lower discharge stream from the decomposition device, a side discharge stream from the decomposition device, and a process water stream to a mixing device and mixing these streams; and
   supplying a discharge stream from the mixing device to a layer separation device to separate the discharge stream from the mixing device into an oil phase and an aqueous phase,
   wherein a portion of an aqueous stream discharged from the layer separation device is supplied to the mixing device, and a residual stream is discharged as waste water including salts.

2. The method of decomposing phenolic by-products of claim 1, wherein the phenolic by-products include any one or more of phenolic by-products produced in a phenol preparation process and phenolic by-products produced in a bisphenol A preparation process.

3. The method of decomposing phenolic by-products of claim 1, wherein the phenolic by-products are a mixture of phenolic by-products produced in a phenol preparation process and phenolic by-products produced in a bisphenol A preparation process.

4. The method of decomposing phenolic by-products of claim 1, wherein the phenolic by-products include one or more selected from the group consisting of bisphenol A, phenol, α-methylstyrene, acetophenone, cumyl phenol, and an α-methylstyrene dimer.

5. The method of decomposing phenolic by-products of claim 1, wherein the materials having a high boiling point are recovered from an oil stream discharged from the layer separation device.

6. The method of decomposing phenolic by-products of claim 1, wherein the effective components include one or more selected from the group consisting of bisphenol A, phenol, α-methylstyrene, and cumene.

7. The method of decomposing phenolic by-products of claim 1, wherein the side discharge stream from the decomposition device includes 40 wt % or more of acetophenone.

8. The method of decomposing phenolic by-products of claim 1, wherein the lower discharge stream from the decomposition device and the side discharge stream from the decomposition device form a mixed stream and the mixed stream is supplied to the mixing device.

9. The method of decomposing phenolic by-products of claim 8, wherein the mixed stream is passed through a cooler before being introduced to the mixing device.

10. The method of decomposing phenolic by-products of claim 1, wherein a flow rate ratio of the lower discharge stream from the decomposition device, the side discharge stream from the decomposition device, and the process water stream is 1:0.2 to 0.8:1 to 3.

* * * * *